(12) United States Patent
Behnsen et al.

(10) Patent No.: US 6,809,862 B2
(45) Date of Patent: Oct. 26, 2004

(54) IN-SITU MICROSCOPE DEVICE REACTORS

(75) Inventors: Wilhelm Behnsen, Wunstorf (DE);
Thomas Scheper, Hannover (DE);
Klaus Joeris, Monchengladbach (DE);
Jorg Schaper, Hannover (DE);
Jan-Gerd Frerichs, Hannover (DE)

(73) Assignee: Jan-Gerd Frerichs, Hannover (DE)

(*) Notice: Subject to any disclaimer, the term of this patent is extended or adjusted under 35 U.S.C. 154(b) by 93 days.

(21) Appl. No.: 10/240,501

(22) PCT Filed: Apr. 4, 2001

(86) PCT No.: PCT/EP01/03817
§ 371 (c)(1),
(2), (4) Date: Oct. 28, 2002

(87) PCT Pub. No.: WO01/77282
PCT Pub. Date: Oct. 18, 2001

(65) Prior Publication Data
US 2003/0147132 A1 Aug. 7, 2003

(30) Foreign Application Priority Data
Apr. 5, 2000 (DE) .......................................... 100 16 838

(51) Int. Cl.[7] ............................................... G02B 21/26
(52) U.S. Cl. ........................ 359/392; 359/368; 359/382
(58) Field of Search ............................... 359/368, 391, 359/398, 385, 38, 9, 390, 392, 363, 382, 383, 507, 513, 509, 512; 356/244, 246; 355/30; 600/100, 109, 121, 130, 156, 157, 158, 160

(56) References Cited

U.S. PATENT DOCUMENTS

| 3,582,181 | A | * | 6/1971 | Manau de Chveca | ....... 359/379 |
| 4,364,629 | A | | 12/1982 | Lang et al. | .................. 359/377 |
| 4,647,540 | A | * | 3/1987 | Ozawa et al. | ............ 435/288.7 |
| 4,661,845 | A | * | 4/1987 | Saito et al. | .................... 348/81 |
| 5,243,409 | A | | 9/1993 | Sagner | ........................ 356/436 |
| 5,369,525 | A | * | 11/1994 | Bala et al. | .................. 359/435 |
| 5,572,370 | A | * | 11/1996 | Cho | ........................... 359/801 |
| 5,863,287 | A | * | 1/1999 | Segawa | ...................... 600/121 |
| 6,313,943 | B1 | * | 11/2001 | Ikado et al. | ................ 359/368 |

FOREIGN PATENT DOCUMENTS

| DE | 35 18 240 A1 | 11/1985 |
| DE | 256 867 A1 | 5/1988 |
| DE | 38 22 451 A1 | 1/1990 |
| DE | 40 32 002 A | 6/1991 |
| EP | 0 497 347 A | 8/1992 |
| WO | 99/36760 A | 7/1999 |

OTHER PUBLICATIONS

Brochure of Mettler–Toledo GmbH "InTrac 796–M; In Trac 796–P Instruction Manual", copyright 12/98.
Brochure of Mettler–Toledo GmbH "InTrac 796 Retractable housing for use in biotechnology", Jan. 2002.

* cited by examiner

*Primary Examiner*—Arnel C. Lavarias
(74) *Attorney, Agent, or Firm*—Nixon & Vanderhye P.C.

(57) ABSTRACT

An in-situ microscope device for reactors, especially bioreactors, having an immersion tube in a reactor connecting port, which, inside the reactor, has an inlet for a sample area, also a microscope outer tube, which is coaxially placed inside the immersion tube and which, on the inner end with the objective, is directed toward the sample area that is located between an objective cover glass and an object support glass body arranged opposite the same. The exterior of the microscope outer tube is connected to a camera for recording the image of the sample area. Also included is a rinsing chamber having closeable openings, through which cleaning agents can be introduced, is connected to the exterior of the reactor connecting port, and that the immersion tube can move in an axial direction inside the connecting port and can be retracted until the inlet is in contact with the rinsing chamber in order to enable a cleaning of the sample area.

20 Claims, 4 Drawing Sheets

IN-SITU MICROSCOPE DEVICE REACTORS

The present invention relates to an in-situ microscope device for reactors, such as for example bioreactors.

BACKGROUND OF THE INVENTION

With such in-situ microscope devices, examinations can be carried out on specimens of the material in the inside of the reactor during ongoing operation, for example the concentration of particular cells in the medium can be monitored. The basic principles of in-situ microscopy for reactors are described in patent specification DE 40 32 002 C2.

An in-situ microscope device with the features of the precharacterizing clause of claim 1 is described e.g. in the dissertation "In-situ-Mikroskopie; Ein neues Verfahren zur Online-Bestimmung der Biomasse bei Kultivierungsprozessen" [In-situ microscopy: a new process for online determination of biomass in cultivation processes], Dr. Christoph Bittner, Hanover, 1994.

The monitoring and controlling of biotechnological processes has gained a major significance in the recent past e.g. in the chemical and pharmaceutical industries. Examples of this are the synthesis of human proteins, such as e.g. interleukin (IL-2), tissue plasminogen activator (t-PA) or antithrombin (AT-III), the preparation of which with the help of organic synthesis can be achieved only with difficulty, with the result that the manufacture of these proteins with the help of the cultivation of mammal cells is preferred. Microorganisms, here in particular yeasts, are used also in the manufacture of products of the food industry, e.g. beer, wine, cheese or bread. Further products or pharmaceuticals are produced by the cultivation of other organisms. In the case of in-situ microscopy, a microscope probe is inserted into a connection port of a fermenter (reactor) in order to monitor and control such processes. This microscope probe enables an image to be photographed directly in the culture stock. The photographed microscope image is photographed and digitized by a CCD camera connected to the in-situ microscope. The evaluation of the digitized microscopic images is carried out with the help of image-processing programs on a standard computer. Information about cell sizes and biomass, cell-size distribution, cell concentration, cell morphology and cell vitality can be obtained using the image data material obtained with the in-situ microscope and analyses applied to it. On the basis of the information, thereby obtained during ongoing operation, about the state of the system located in the reactor, process parameters can be influenced and controlled in order to achieve a desired development of the system.

An in-situ microscope for the observation of cultivation processes in yeasts is described in the above-mentioned dissertation by Bittner. The microscope has a dip tube which is inserted into a reactor connection port. In the end-section of the dip tube lying in the inside of the reactor, an inlet is provided through which the culture medium can flow freely. A microscope external tube is arranged coaxially in the dip tube and, with its lens lying at the inner end, is directed towards a specimen zone which is defined between the cover glass of the lens and a slide glass body lying opposite. Connected to the opposite end is the microscope external tube with a camera for photographing the image of the specimen zone. If the specimen zone is open, the lens cover glass and the slide glass body lying opposite lie at some distance from each other, the culture medium from the inside of the reactor being able to flow freely through this space. In order to photograph the image, the specimen zone is closed by moving the slide glass body onto the lens cover glass until a sealing ring surrounding the slide glass body comes to rest against the lens cover glass and thus creates a specimen zone with a defined volume between the slide glass body and the lens cover glass. In the known device, the specimen zone is closed by pulling the slide glass body with an illumination unit below it against the lens. This movement is achieved via a pull rod which runs in longitudinal direction in the dip tube alongside the microscope external tube, and is connected at one end to the unit of the slide glass body and at the other end to a drive outside the dip tube. Furthermore, a wiping apparatus is provided with which the lens cover glass is intended to be cleaned by wiping off if required. Such a wiping apparatus is necessary as the glass rapidly becomes dirty and another cleaning method cannot be carried out at all while cultivation is in progress and, even after the cultivation process is stopped, can be carried out only if considerable effort is expended and the microscope is completely removed from the reactor. The wiper is also driven by an external drive via a mechanical power transmission means.

The known in-situ microscope device is disadvantageous in various respects. For example, it is disadvantageous that mechanical power transmission means alongside the microscope tube must be guided through the dip tube, as this restricts the space available for the microscope tube. Furthermore, such mechanical power transmission means are costly in design terms and are incident-prone.

However, the main disadvantage of the known in-situ microscope devices is that the microscope is not accessible while cultivation is in progress because, if the reactor is opened by removing the dip tube or by pulling out the microscope, the cultivation would be contaminated. Furthermore, if the microscope was installed at the side, the reactor would first have to be emptied, which for practical use is out of the question.

The removability of the microscope is of significance not only for cleaning purposes during the operation, but also for the sterilization/autoclaving of the reactor system before commissioning, as temperatures of over 120° C. are used.

For industrial-scale applications of in-situ microscopy, microscope devices are required which are robust, flexible and easy to handle.

The object of the present invention is therefore to create an in-situ microscope device, the sensitive parts of which are accessible at any time, without having to interrupt the cultivation process or endangering it through a contamination.

The characterizing features of patent claim 1 in conjunction with its precharacterizing clause serve to achieve this object. Advantageous versions of the invention are listed in the dependent claims.

BRIEF DESCRIPTION OF THE INVENTION

According to the invention, it is provided that the dip tube is guided movable in axial direction in the reactor connection port, to which a rinsing chamber with sealable openings is externally connected, through which cleaning agents can be fed in. The dip tube can be pulled back into the connection port until the inlet of the dip tube communicates with the rinsing chamber. Sealing means are provided at the dip tube in order to keep the internal space of the reactor sealed off from the rinsing chamber when the dip tube is pulled back into the rinsing chamber. In this way, the specimen zone can be cleaned, when the dip tube is pulled back into the rinsing chamber, by feeding cleaning agents into the rinsing chamber. The internal space of the reactor remains sealed off from the inside of the rinsing chamber in order that the specimen zone can also be cleaned while cultivation is in progress, without the danger of contamination.

Furthermore, the microscope external tube can be pulled out when the dip tube is pulled back into the rinsing chamber. Thereby, all parts of the microscope device which are arranged inside the dip tube can be removed and if necessary replaced or repaired, without the sterile barrier to the inside of the reactor being broken through. Thereby, changes to the design and fitting of the microscope, maintenance work and the like can also be carried out during ongoing operation of the reactor, without the cultivation process in the reactor having to be interrupted, or the danger(of contamination. Thereby, handling during ongoing operation, operational reliability and variability can be decisively improved by replacing components of the microscope, with the result that the in-situ microscope device is particularly well-suited to industrial applications due to its flexibility and robustness.

In an advantageous version, there is accommodated in the end of the dip tube pointing towards the inside of the reactor an illumination unit which carries the slide glass body and has a light source in order to illuminate the specimen zone through the slide glass body.

In an advantageous version, the microscope external tube is for its part housed in a microscope-housing tube, wherein the microscope-housing tube is closed at the end facing the inside of the reactor except for an inlet for specimen material and surrounds the specimen zone from the rear, and wherein the illumination unit is arranged at the inward-lying end of the microscope-housing tube. The microscope external tube is advantageously housed movable in axial direction in the microscope-housing tube and a drive is provided which acts on the outward-lying end of the microscope external tube. The microscope external tube can be moved relative to the microscope-housing tube by the drive, in order thus to be able to open and close the specimen zone between the lens cover glass at the microscope external tube and the slide glass body of the illumination unit by pushing forward and pulling back the microscope external tube controlled by the drive. Alternatively, at the inner end of the microscope-housing tube a drive can be provided which acts on the illumination unit housed movable in axial direction in the microscope-housing tube, in order to be able to open and close the specimen zone by moving the illumination unit. Particularly advantageously, a step motor or a regulated direct-current motor is used as a drive, whereby a very precise setting of the specimen zone can be achieved.

In an alternative version, the illumination unit and the microscope external tube form two separate units which are not housed as above in a common microscope-housing tube, the illumination unit being arranged at the inner end of the dip tube and the microscope external tube being housed movable in axial direction directly in the dip tube, the microscope-housing tube in the version described above thus being dispensed with. Furthermore, a drive is provided which acts on the end, lying outside the reactor, of the microscope external tube in order to move this relative to the dip tube in a controlled manner, in order thus to be able to open and close the specimen zone between the lens cover glass at the microscope external tube and the slide glass body of the illumination unit by pushing forward and pulling back the microscope external tube.

In all versions, it can be provided that a microscope tube is housed movable in the microscope external tube and that a drive means is provided in order to be able to move the microscope tube in longitudinal direction in a controlled manner, in order thus to be able to set the lens against the microscope tube relative to the specimen zone for focusing.

With the previously described forms, it is possible to exploit the cross-section available in the dip tube as far as possible, because no drive transmissions need to be guided through the dip tube. Furthermore, the position of the slide glass body and the lens cover glass relative to each other, which between them form the specimen zone, can be set very accurately in a controlled manner by the drive.

The fact that the cross-section area of the dip tube can be fully exploited, because no drive transmissions need to be guided through, means that dip tubes with a relatively small internal diameter, into which a microscope external tube is introduced, can also be used. In this way, dip tubes of conventional, standardized exchangeable probe systems, in which the external diameter of the probe to be used is limited, can also be used.

If the dip tube is pulled back into the rinsing chamber, cleaning agents, e.g. superheated steam, can be fed in through the sealable openings of the rinsing chamber in order that in this way the cleaning agents enter the specimen zone through the inlet of the dip tube, in order to clean the specimen zone. If the dip tube is pulled back until its inlet communicates with the rinsing chamber, the inside of the reactor is sealed off and the inlet of the dip tube lies in the inside of the rinsing chamber and no longer communicates with the inside of the reactor. In this situation, the microscope external tube or the microscope-housing tube can be pulled out of the dip tube. All essential parts of the microscope are thereby accessible and can be repaired or varied by replacing components. The last-mentioned possibility of changing the properties of the microscope by replacing components also applies to the specimen zone, because e.g. the slide glass body can be replaced in order to obtain another geometric definition of the specimen zone.

If a drive is provided in order to set the specimen zone by moving the microscope external tube or the illumination unit relative to each other, an accurate definition of the specimen zone is possible through such a precisely controllable drive. The motor control allows a variable configuration of the specimen zone, i.e. the height of the specimen zone to be selected through variable approaching. A supplementary or alternative option of a variable configuration of the specimen zone is offered by particular forms of the slide glass body which are described in the following.

In this regard, it is preferred in particular that the slide glass body has a sapphire glass plate with a level external area, on the circumference of which an annular rim of a predefined thickness is formed which serves as a spacer if the lens cover glass is moved against the slide glass body until it rests against the annular rim in order to close the specimen zone. By keeping ready slide glass bodies with annular rims of various thicknesses, the height of the specimen zone can be varied by using a selected slide glass body. The annular rim can be formed e.g. by the polishing in of a recess into a sapphire glass plate or produced by applying an annular material layer.

Instead of an annular spacer, several discrete spacer bodies can also be formed on the sapphire glass plate, e.g. two oblong spacers which between them form a channel-shaped recess open at both sides. In versions in which several discrete spacers are provided at a distance from each other on the slide glass body, the specimen zone is open at the side opposite the surrounding medium in order that cells can flow continuously through the specimen zone and therefore the image recorded by the microscope continuously changes. A higher measuring frequency can thus be achieved by the photographing of image sequences because the specimen zone need not be opened and closed for each image, rather a complete replacement of the medium in the specimen zone should be effected by the opening of this only at certain intervals. This version of the specimen zone differs significantly from the specimen zones closed on all sides, which serve exclusively to keep the specimen steady in the specimen zone. The opposite is the case in the variant proposed here. When using LEDs of high light intensity for illumination, the exposure time of the camera can be shortened such that the cells are represented sharply despite their movement.

The in-situ microscope device according to the invention can operate with a finite or an infinite lens.

Furthermore, in addition to the already-described operating method of transillumination bright-field microscopy, the in-situ microscope device can also be used with an illumination unit below the specimen zone for direct-light dark-field microscopy or for direct-light bright-field microscopy.

BRIEF DESCRIPTION OF THE DRAWINGS

The invention is described in the following with reference to an embodiment in the drawings in which.

DETAILED DESCRIPTION OF THE INVENTION

Figure 1:
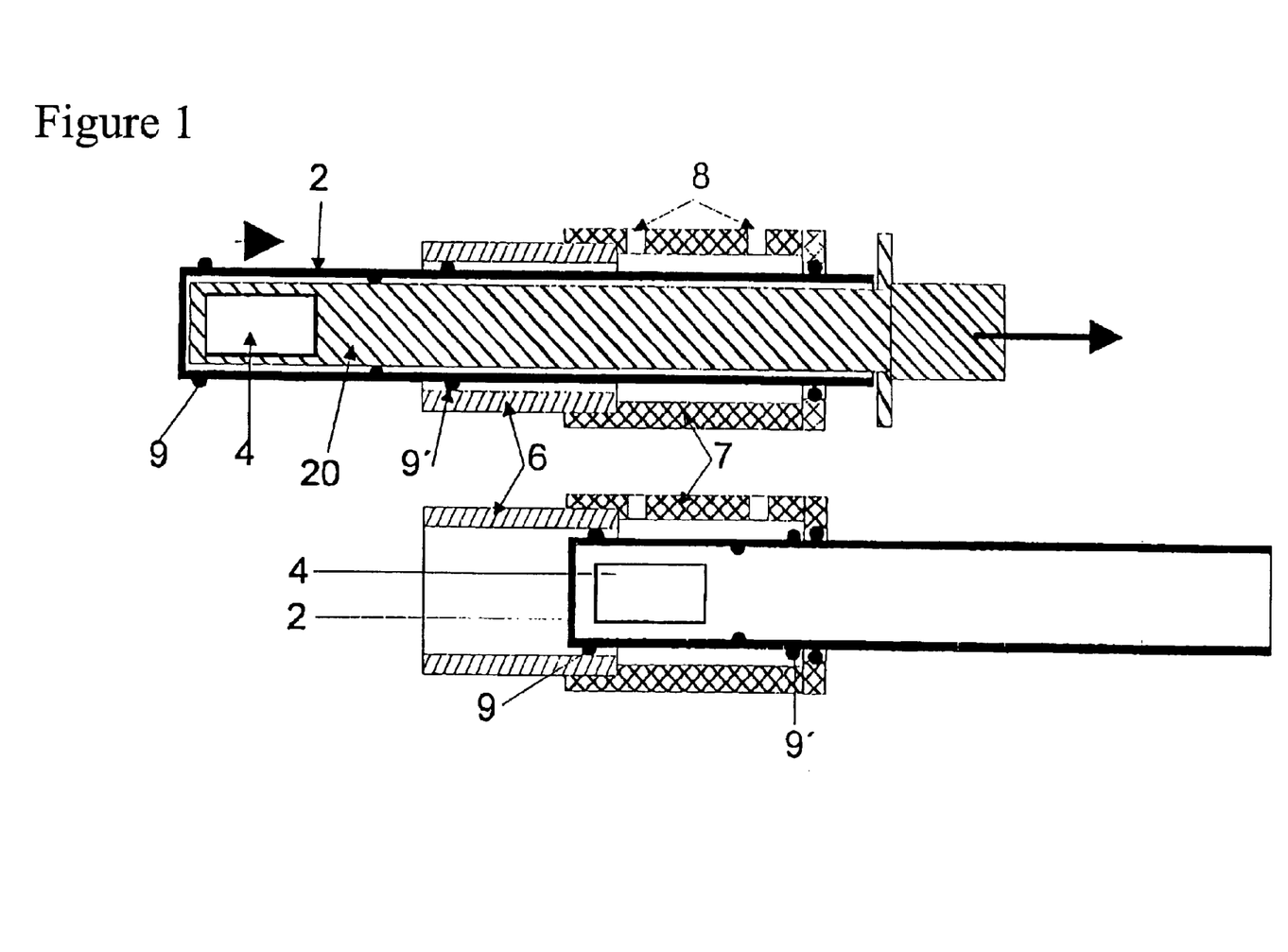
FIG. 1 shows a partial-section view of an in-situ microscope device in operating position in the reactor (above) and in pulled-back position (below) of the dip tube in the reactor connection port, the microscope-housing tube being removed from the dip tube in the lower representation.
Figure 2:
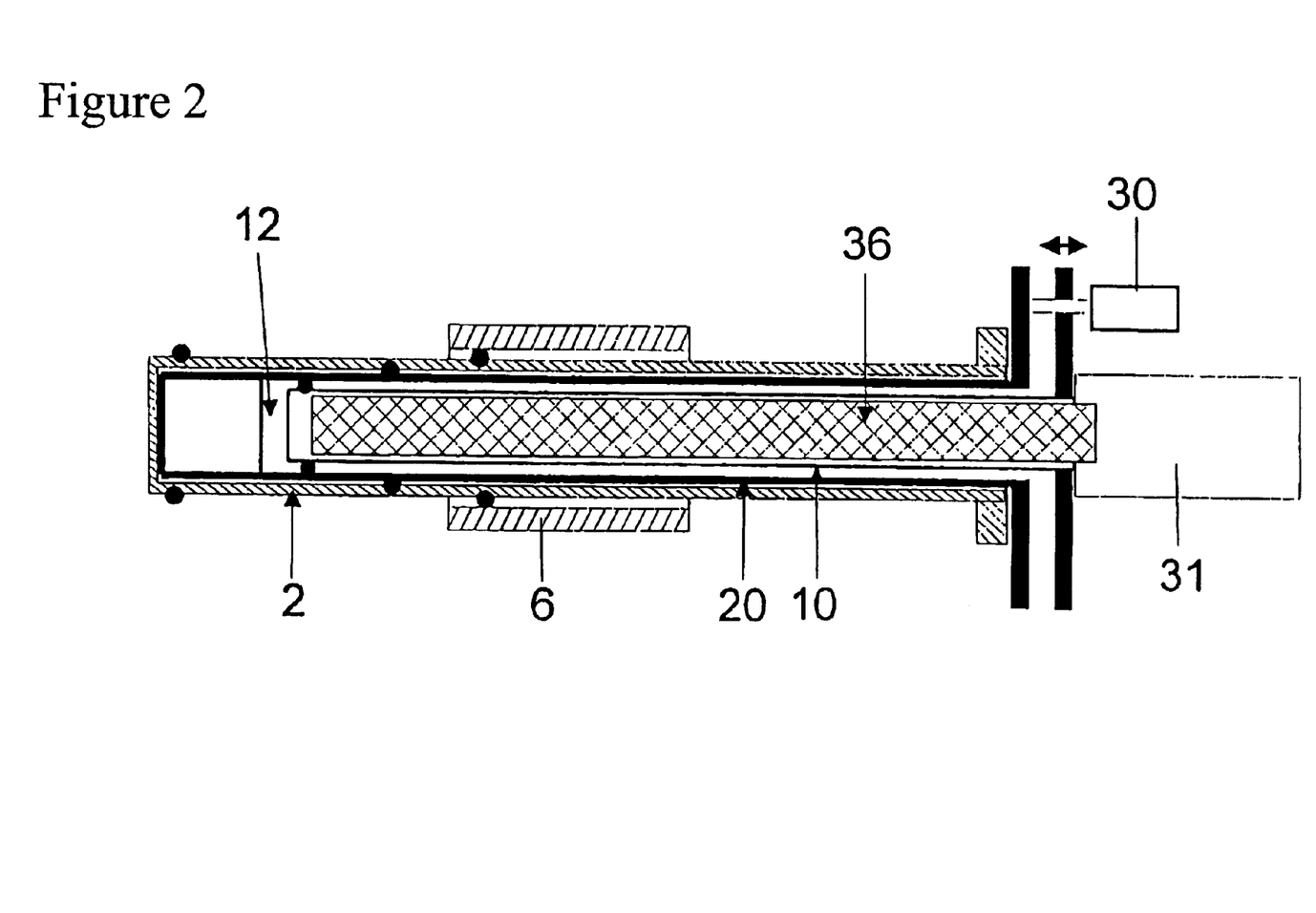
FIG. 2 shows a partial-section view of the version from FIG. 1, the microscope external tube being represented arranged in the microscope-housing tube.

The version of the in-situ microscope device represented schematically in section in the FIGS. 1 and 2 has a dip tube 2 which is inserted into a reactor connection port 6 which is firmly connected to the reactor wall (not shown). In FIG. 2, in order to simplify the representation, the rinsing chamber 7 against the reactor connection port 6 is not shown. In the position represented above in FIG. 1, the dip tube 2 with its inlet 4 lies inside the reactor in order that the medium in the inside of the reactor can flow through the inlet 4 through the specimen zone of the in-situ microscope device. Connected outside to the reactor connection port 6 is a rinsing chamber 7 which rests at its external end with seals against the outer surface of the dip tube 2. The dip tube 2 can be pulled back through the reactor connection port 6 until the inlet 4 communicates with the rinsing chamber 7, as represented in FIG. 1 below. In this position, seals 9 running round outside at the circumference, which rest against the inner wall of the reactor connection port, seal off the inside of the reactor so that there is no longer a connection between the inlet 4 of the dip tube and the inside of the reactor. Cleaning agents, e.g. superheated steam, can be fed in through the sealable openings 8 of the rinsing chamber 7 in order to clean the specimen zone.

The microscope-housing tube 20 is housed movable in the dip tube. In the position represented below in FIG. 1, the microscope-housing tube is removed from the dip tube with the result that all parts of the microscope located therein can be handled for maintenance or for the replacement of components. At the same time, the inside of the reactor is sealed off by the dip tube 2 in the connection port 6 with the result that the inside of the reactor cannot be contaminated and the cultivation process can continue.

As represented in FIG. 2, there is located in the microscope-housing tube 20 a microscope external tube 10 which is housed movable therein. The microscope-housing tube 20 likewise has an inlet which communicates with the inlet 4 of the dip tube with the result that the medium in the inside of the reactor can flow through the specimen zone 12.

Outside the reactor a drive 30 is provided, e.g. a step motor, which provides a drive between microscope-housing tube 20 and microscope external tube 10 in order to move the latter relative to the microscope-housing tube. Through the movability of the microscope external tube 10, in this version the movement is realized which is used to open and close the specimen zone, the specimen zone being defined between a slide glass body which during operation is arranged fixed in the lower section of the dip tube, and the lens cover glass which is arranged at the end of the movable microscope external tube 10. Through the movable housing of the microscope external tube 10 and the provision of a drive 30 in order to move the microscope external tube 10 so as to open and close the specimen zone, the cross-section area in the microscope-housing tube 20 can be fully exploited for the microscope external tube 10, because no mechanical drive transmissions whatsoever into the front section of the specimen zone are required.

The drive 30 engages on one side at a pusher of the microscope-housing tube 20 and on the other side at a pusher of the microscope external tube 10 in order to move these relative to each other. The size of the specimen zone, i.e. the distance between the slide glass body at the illumination unit and the lens cover glass at the microscope external tube 10, is defined by the position of the microscope external tube 10 relative to the microscope-housing tube 20.

As a drive 30 a step motor is preferably used, which opens up the possibility of being able to precisely adapt the specimen zone with variable height to the respective requirements in a specific situation. However, in principle any drive means is possible for the drive 30, thus e.g. pneumatic drive means or a piezomodule can also be used for the drive 30. The motor control allows the specimen zone to be set in a variable manner, i.e. the height of the specimen zone to be selected through variable approaching. A further possibility of realizing variable specimen zones consists of providing slide glass bodies with selected spacers which define the distance from the lens cover glass, as described further below in connection with FIG. 4.

At the outer end, the microscope external tube 10 is connected to a camera 31, e.g. a CCD camera, which records the microscope image of the specimen zone.

The version represented in FIGS. 1 and 2 has the advantage that by pulling out the microscope-housing tube 20 the whole microscope can be removed as a unit from the dip tube if the dip tube is pulled back into the position represented below in FIG. 1, without adversely affecting the sterile conditions in the inside of the reactor, because the inside of the reactor is kept sealed off by the inner end of the dip tube and the seals 9, 9'.

Located in the microscope-housing tube below the specimen zone 12 (FIG. 2) is an illumination unit which has a light source, if necessary lenses, and the slide glass body at the end facing towards the specimen zone 12.

Figure 3:
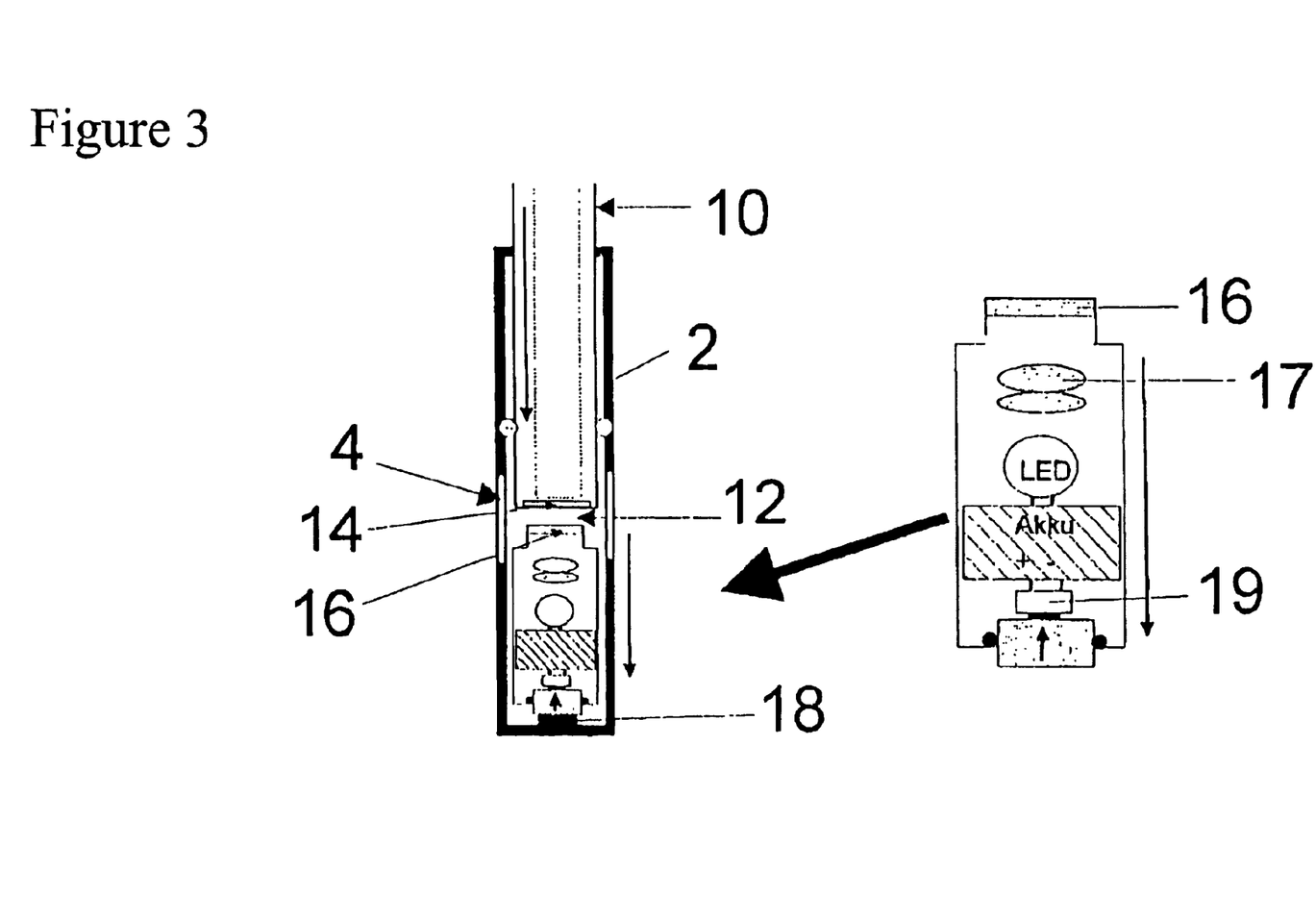
FIG. 3 shows a sectional representation of an alternative version of the in-situ microscope including an enlarged sectional representation of an illumination unit.

FIG. 3 shows a partial view of a further version in section, only the dip tube 2 with the lens end of the microscope external tube 10 inserted therein being represented here, while the reactor connection port and the rinsing chamber are omitted in order to simplify the representation. There is no microscope-housing tube in this version. Instead of this, the illumination unit and the microscope external tube 10 are housed directly in the dip tube 2. The illumination unit is located in the end of the dip tube lying in the inside of the reactor and is kept detachable by a magnet 18 at the base of the dip tube. The illumination unit has a contact body housed movable therein, which rests on the magnet 18. The movable contact is in contact with a switch 19 in the inside of the illumination unit. The switch 19 is connected to a power source, e.g. an accumulator, and connects the power source to the light source when the switch is triggered, preferably to a light-emitting diode (LED). Above the light source lies a condenser 17 and above this a slide glass body 16 which is designed as a sapphire plate.

If the specimen zone 12 is closed, the microscope external tube 10 is moved towards the illumination unit by a drive until the lens cover glass 14 comes into contact with points provided for this on the slide glass body 16. Thereby the illumination unit as a whole is pressed towards the base of the dip tube, whereby the movable contact body acts on the switch 19 and the light source is activated if the specimen zone 12 is closed. As the light source is switched on only if the specimen zone 12 is closed, power consumption is minimal. The fixing of the illumination unit to the base of the dip tube 2 by a securing apparatus, e.g. a magnet, is important in order that the illumination unit does not detach itself from the base if the specimen zone 12 is opened (this could otherwise occur due to adhesive forces which act between the lens cover glass 14 and the slide glass body 16 and the liquid film enclosed by these). The illumination unit is provided with recesses at its end facing the specimen zone in order that they do not completely fill the cross-section of the dip tube 2 there. As a result of these recesses, the illumination unit can be grasped with a special tool, for example tongs, and removed from the dip tube 2 if the dip tube 2 is in the pulled-back position in the reactor connection port and the rinsing chamber, and the microscope external tube 10 is pulled out of the dip tube 2.

As a result of the invention, it is possible during the ongoing cultivation process to pull back the dip tube into the reactor connection port and to remove the microscope components, whereby in particular the specimen zone can be varied by replacing components, e.g. the slide glass body.

In FIG. 3, the slide glass body 16 is merely represented schematically as a sapphire glass plate. For an exactly defined specimen zone to be formed between the lens cover glass 14, the outer surface of which is level, and the surface of the slide glass body 16, the slide glass body 16 can be provided on its outer surface with spacers which come to rest against the lens cover glass 14 if the specimen zone is closed, with the result that an intermediate layer of a defined thickness is formed.

In order to realize such spacers, e.g. an annular structure can be mounted on the plate-shaped slide glass body, wherein this ring body should be formed from biocompatible material and should not be compressible.

Figure 4:
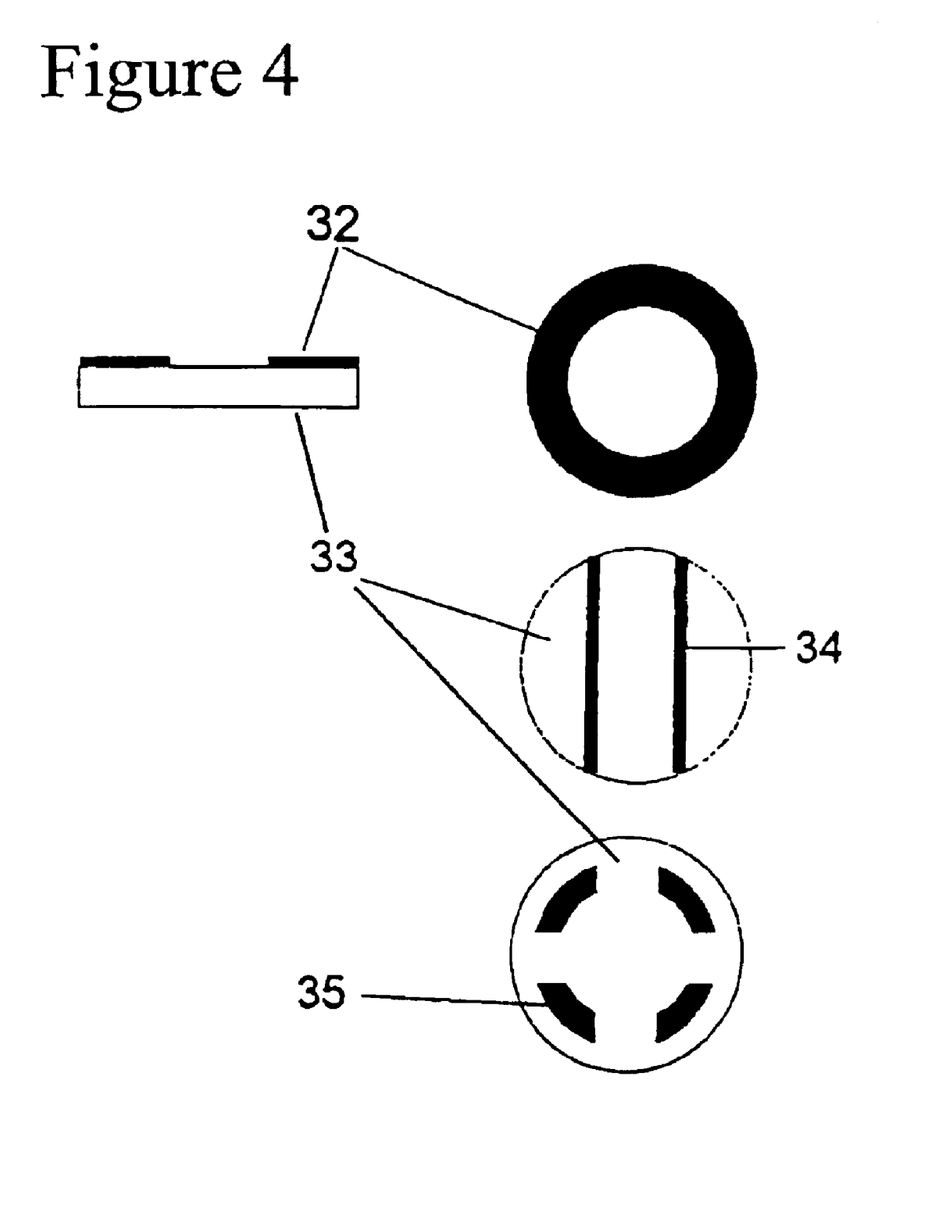
FIG. 4 represents various versions of a slide glass body.

In FIG. 4, such a ring body has the reference number 32. Such a ring body 32 of a predefined thickness can be formed e.g. by evaporating material onto the sapphire glass plate 33. The ring body 32 can also be formed by the polishing in of a recess. Furthermore, the ring body can also be cut out from high-grade steel foils or plastic foils and mounted on the glass plate. In principle, it is also possible to form the ring by evaporating sapphire onto the sapphire glass plate 33. In all cases, the ring body 32 can be formed with a predefined thickness with the result that a specimen zone of a predefined height is defined which is determined as a spacer by the thickness of the ring body 32. Thereby any height of specimen zone can be predefined, and this height can be changed relatively easily (by replacing the ring body) or by completely replacing the slide glass body.

The method of manufacturing an external ring body by the polishing in of a recess is more economical than evaporation, but is less accurate. Furthermore, during the polishing in of the recess, scratches can occur which can disrupt the photographing of the image. In typical cases, the recess is formed with a depth of 40 $\mu$m.

In the case of the prescribed specimen zones with an external ring body as a spacer, the volume of the specimen zone is closed off from the surrounding culture medium if the lens cover glass is brought up, because the lens cover glass rests against the ring body and this is closed at the circumference. In this way, the medium is kept steady in the specimen zone.

In another form of the specimen zone, this can be defined by a plurality of separate spacers 34 or 35, as represented below in FIG. 4. E.g. two rectilinear spacers 34 can be provided which between themselves enclose a channel-shaped zone above the surface of the slide glass body 33, the ends of the channel-shaped zone being open. In this way, if the lens cover glass comes to rest against the rectilinear spacers 34, an open specimen zone is formed. The cells of the culture medium can flow through this open specimen zone. The composition of the specimen-zone content therefore changes constantly. The same applies to versions with several spacers 35 which are arranged at the circumference of a ring on the sapphire glass plate 33, but have several breaks with the result that the specimen zone is likewise designed to be open.

By photographing image sequences in open specimen zones a much higher measuring frequency can be realized, which can be of significance when measuring rapidly-growing organisms. The higher measuring frequency is possible because the specimen zone need not be opened and closed for every image in the sequence, rather a complete replacement of the contents of the specimen zone is carried out by opening and closing the specimen zone only after specific longer periods. This version of the specimen zone clearly differs from the previously-described specimen zones which serve exclusively to keep the cells in the specimen zone steady. In the case of the open specimen zones, the opposite is achieved and this enables a constant flow through the specimen zone to be maintained in order to avoid blockages or deposits and to guarantee representative specimens. When using light sources of high light intensity, the exposure time of the CCD camera can be shortened to the extent that the cells are represented sharply despite the movement.

In all versions of the invention, a microscope tube which carries the lens at its front end can be housed movable within a microscope external tube 10, with the result that the microscope tube can be moved and set relative to the lens cover glass 14 on the microscope external tube 10 by drive means, in order thereby to enable a focusing. The microscope tube has the reference number 36 in FIG. 2.

With the illumination unit described above, the in-situ microscope device is used for transillumination bright-field microscopy. Alternatively, an illumination can be provided which facilitates a direct-light darkfield microscopy. Such illumination can be realized e.g. by the presence outside the dip tube of an external light source, the light from which is coupled into light guides which, within the microscope external tube, are guided inwards to the lens end and guided through a mounting ring encompassing the lens. The light-radiating end-surfaces of the light guides are aligned at the mounting ring such that the radiated light is directed obliquely onto the slide glass body with the result that no direct or reflected light, but only light scattered by the measuring objects, enters the lens, as is necessary in the case of darkfield microscopy. Alternatively, the light-radiating end-surfaces of the light guides can be set with their angles of radiation such that the emerging light evenly illuminates the field of view, as is necessary for direct-light bright-field illumination. Furthermore, by providing a monochromatic light source and a blocking filter in front of the camera, an epi-fluorescence illumination can also be achieved in the direct light.

What is claimed is:

1. In-situ microscope device for reactors, with a dip tube which is insertable into a reactor connection port and has an inlet, in the end-section pointing to the inside of the reactor, for a specimen zone, and a microscope external tube, arranged coaxially in the dip tube, which at the inner end is directed with a lens towards the specimen zone which lies between a lens cover glass and a slide glass body lying opposite in the dip tube, and at the opposite end is coupled with a camera, lying outside the dip tube, for photographing the image of the specimen zone, the lens cover glass and the slide glass body being movable relative to each other, in order to be able to open and close the specimen zone, characterized in that connected outside to the reactor connection port (6) is a rinsing chamber (7) with sealable openings (8) through which cleaning agents can be fed in, and the dip tube (2) is movable in axial direction in the connection port (6) and can be pulled back until the inlet (4) communicates with the rinsing chamber (7) in order to be able to clean the specimen zone, sealing means (9, 9') being provided at the dip tube in order to keep the internal space of the reactor sealed off from the rinsing chamber (7) if the dip tube is pulled back to the rinsing chamber.

2. In-situ microscope device according to claim 1, characterized in that there lies, at the end of the dip tube pointing to the inside of the reactor, an illumination unit which carries the slide glass body and has a light source in order to illuminate the specimen zone through the slide glass body.

3. In-situ microscope device according to claim 2, characterized in that there is arranged in the dip tube (2) a microscope-housing tube (20) housing the microscope external tube (10), wherein the microscope-housing tube (20) is closed at the end facing the inside of the reactor except for an inlet for specimen material and surrounds the specimen zone from the rear, and wherein the illumination unit is arranged at the inward-lying end of the microscope-housing tube (20).

4. In-situ microscope device according to claim 3, characterized in that the microscope external tube (10) is housed movable in axial direction in the microscope-housing tube (20) and a drive (30) is provided which acts on the end, lying outside the reactor, of the microscope external tube (10) in order to move this relative to the microscope-housing tube (20) with the result that the specimen zone (12) can be closed and opened between the lens cover glass (14) and the slide glass body (16) of the illumination unit by pushing forward and pulling back the microscope external tube (10).

5. In-situ microscope device according to claim 3, characterized in that the illumination unit is housed movable in axial direction in the microscope-housing tube (20) and, below the illumination unit, a drive is provided in the microscope-housing tube (20), with the result that the specimen zone (12) between the lens cover glass (14) and the slide glass body (16) can be closed and opened by moving the illumination unit.

6. In-situ microscope device according to claim 2, characterized in that the illumination unit is detachably attached as a separate unit to the base of the dip tube (2), the microscope external tube (10) is housed movable in axial direction directly in the dip tube (2) and a drive (30) is provided which acts on the end, lying outside the reactor, of the microscope external tube (10) in order to move this relative to the dip tube (2), with the result that the specimen zone (12) between the lens cover glass (14) and the slide glass body (16) of the illumination unit can be closed and opened by pushing forward and pulling back the microscope external tube (10).

7. In-situ microscope device according to claim 4, characterized in that the drive comprises a step motor or a regulated direct-current motor.

8. In-situ microscope device according to claim 6, characterized in that a magnet is provided which keeps the illumination unit detachable at the base of the dip tube (2).

9. In-situ microscope device according to claim 8, characterized in that the illumination unit has a push button (19) which is arranged such that, when closing the specimen zone, it is triggered by the moving of the microscope external tube up against the illumination unit in order to switch on a light.

10. In-situ microscope device according to claim 6, characterized in that the illumination unit at the end of the slide glass body does not completely fill the cross-section area of the dip tube, with the result that the illumination unit can be grasped from above by a tool in order to remove it from the dip tube.

11. In-situ microscope device according to claim 1, characterized in that a microscope tube is housed movable in the microscope external tube and a drive means is provided in order to move the microscope tube in longitudinal direction in a controlled manner, in order to be able to set the lens against the microscope tube relative to the specimen zone for focusing.

12. In-situ microscope device according to claim 1, characterized in that the slide glass body has a sapphire glass plate with a level outer surface on which on the circumference an annular rim of a predefined thickness is formed, which serves as a spacer if the lens cover glass is moved up against the annular rim, in order to close the specimen zone.

13. In-situ microscope device according to claim 12, characterized in that the annular rim is formed by the polishing in of a recess into a sapphire glass plate.

14. In-situ microscope device according to claim 12, characterized in that the annular rim (32) is formed by applying an annular material layer.

15. In-situ microscope device according to claim 1, characterized in that the slide glass body has a sapphire glass plate with a level external area on which a plurality of spacers of the same, predefined thickness is formed which serve as spacers if the lens cover glass is moved up against the slide glass body until it rests against the spacers in order to close the specimen zone.

16. In-situ microscope device according to claim 15, characterized in that the slide glass body (16) has on the outer surface two spacers (34) which between them form a channel-shaped recess open on both sides.

17. In-situ microscope device according to claim 2, characterized in that the illumination unit comprises a light-emitting diode as a light source.

18. In-situ microscope device according to claim 1, characterized in that, to operate the microscope for direct-light darkfield microscopy, an external light source arranged outside the dip tube as well as light guides are provided, which are arranged such that they receive light from the light source and guide it to a mounting ring, encompassing the lens, from which their light-radiating end-surfaces project, in order to direct the emerging light onto the surface of the slide glass body in such a way that no direct or reflected light, but only light scattered by the measuring objects in the specimen zone, enters the lens.

19. In-situ microscope device according to claim 1, characterized in that, to operate the microscope for direct-light bright-field microscopy, an external light source arranged outside the dip tube as well as light guides are provided, which are arranged such that they receive light from the light source and guide it to a mounting ring, encompassing the lens, from which their light-radiating end-surfaces protect, the angle of radiation being chosen such that the emerging light evenly illuminates the field of view, as is necessary for direct-light bright-field illumination.

20. In-situ microscope device according to claim 19, characterized in that a monochromatic light source is used and a blocking filter is arranged in front of the camera in order to enable an epi-fluorescence illumination in the direct light.

* * * * *